(12) United States Patent
Spendler et al.

(10) Patent No.: US 7,033,626 B2
(45) Date of Patent: Apr. 25, 2006

(54) PRODUCTION OF EDIBLE PRODUCTS

(75) Inventors: Tina Spendler, Malov (DK); Hans Peter Heldt-Hansen, Virum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/493,682

(22) PCT Filed: Oct. 10, 2002

(86) PCT No.: PCT/DK02/00641

§ 371 (c)(1),
(2), (4) Date: Apr. 23, 2004

(87) PCT Pub. No.: WO03/034838

PCT Pub. Date: May 1, 2003

(65) Prior Publication Data

US 2004/0265428 A1    Dec. 30, 2004

Related U.S. Application Data

(60) Provisional application No. 60/347,574, filed on Jan. 11, 2002.

(30) Foreign Application Priority Data

Jan. 14, 2002  (DK) ............................... 2002 00051
Oct. 10, 2002  (DK) ............................... 2001 01574

(51) Int. Cl.
*A21D 8/04*  (2006.01)

(52) U.S. Cl. .................. 426/18; 426/549; 426/559; 426/560; 426/439; 426/446; 426/450; 426/458

(58) Field of Classification Search ................. 426/52, 426/20, 28, 18, 549, 559, 560, 653, 439, 426/440, 445, 446, 448, 450, 457, 458
See application file for complete search history.

(56) References Cited

U.S. PATENT DOCUMENTS

| | | | | |
|---|---|---|---|---|
| 5,176,927 A | * | 1/1993 | Haarasilta et al. | 426/20 |
| 5,200,215 A | * | 4/1993 | Slade et al. | 426/18 |
| 5,391,371 A | * | 2/1995 | Jacobsen et al. | 424/94.2 |
| 5,720,971 A | * | 2/1998 | Beauchemin et al. | 424/438 |
| 5,747,092 A | | 5/1998 | Carey et al. | |
| 5,792,499 A | * | 8/1998 | Atwell | 426/549 |
| 5,874,274 A | * | 2/1999 | Jakobsen et al. | 435/200 |
| 5,942,273 A | | 8/1999 | Mochizuki et al. | |
| 6,136,772 A | * | 10/2000 | De Lima et al. | 510/392 |
| 6,291,008 B1 | * | 9/2001 | Robie et al. | 426/620 |
| 6,475,546 B1 | * | 11/2002 | Harz et al. | 426/516 |
| 6,479,090 B1 | * | 11/2002 | Carey et al. | 426/559 |
| 6,500,426 B1 | * | 12/2002 | Barendse et al. | 424/94.1 |
| 6,500,463 B1 | * | 12/2002 | van Lengerich | 424/499 |
| 6,562,340 B1 | * | 5/2003 | Bedford et al. | 424/94.61 |
| 6,764,699 B1 | * | 7/2004 | Rubio et al. | 426/52 |

FOREIGN PATENT DOCUMENTS

WO    WO 98/23162    6/1998

* cited by examiner

*Primary Examiner*—Keith Hendricks
(74) *Attorney, Agent, or Firm*—Jason Isaac Garbell

(57) ABSTRACT

In the production of edible products which includes a holding period for starch retrogra-dation, the addition of a xylanase to cereal-based raw materials accelerates the retrogradation and thus allows a shortening of the holding period.

13 Claims, No Drawings

PRODUCTION OF EDIBLE PRODUCTS

CROSS-REFERENCE TO RELATED APPLICATIONS

This application is a 35 U.S.C. 371 national application of PCT/DK02/00641, filed Oct. 10, 2002, which claims priority or the benefit under 35 U.S.C. 119 of Danish application nos. PA 2001 01574, filed Oct. 26, 2001, and PA 2002 00051, filed Jan. 14, 2002, and U.S. provisional application No. 60/347,574, filed Jan. 11, 2002, the contents of which are fully incorporated herein by reference.

FIELD OF THE INVENTION

The present invention relates to the preparation of an edible product from cereal-based raw materials and water by heating, cooling, holding and drying.

BACKGROUND OF THE INVENTION

The preparation of some cereal-based food products includes a holding step (sometimes known as tempering or ageing) intended to make the starch retrograde sufficiently to make the product acceptable for further processing. This may typically involve holding from 10 to 48 hours at room temperature.

An example is the production of certain snack products (sometimes called third-generation or 3G snacks) in a process including extrusion cooking, followed by cooling, holding and drying to make snack pellets which are expanded by heating (e.g. by frying In oil) to make the final snack product.

Another example is shredded cereals made by cooking whole grain (particularly wheat), followed by cooling, tempering, shredding, forming into biscuits and baking.

The ageing step is by nature a time and space consuming step, and a shortening of this step will give significant advantages to manufactures such as the possibility of reducing floor and rack space or increase production.

SUMMARY OF THE INVENTION

The inventors have found that in the production of edible products which includes a holding period for starch retrogradation, the addition of a xylanase to cereal-based raw materials accelerates the retrogradation and thus allows a shortening of the holding period.

Accordingly, the invention provides a process for producing an edible product, comprising the following sequential steps:
a) mixing a xylanase with cereal-based raw materials,
b) heating so as to gelatinize starch,
c) cooling,
d) holding to effect retrogradation of the starch, and
e) heating.

DETAILED DESCRIPTION OF THE INVENTION

Food Product

The food product may be snack pellets, a snack product (e.g. a third-generation snack), or shredded cereal (e.g. shredded wheat) for use as a breakfast cereal.

Snack Pellets and Products

According to the invention, snack pellets may be produced by a process comprising the following sequential steps:
a) mixing a xylanase with cereal-based raw materials,
b) extruding and heating the mixture so as to gelatinize starch,
c) cooling and holding to effect retrogradation of the starch, and
d) heating and drying.

The raw material mixture typically contains up to 32% water (e.g. 20–32%), and may optionally be preconditioned by heating, e.g. up to 95° C. for 20–240 seconds.

The extrusion cooking may be done in a single-screw or double-screw extruder with a residence time of 30–90 seconds. The extruder will typically comprise a cooking zone at 80–150° C. and a forming zone at 65–90° C. After the extrusion with heating, the mixture will be formed into long rods, typically having a temperature of 60–100° C. (particularly 70–95° C.) and a moisture content of 25–30% or 20–28%. The holding (also termed aging) may take 8–24 hours (particularly 10–16 hours). Before or during the holding, the rods will be cooled, typically to 15–30° C. The holding serves to affect at least partial retrogradation of the starch, either of the amylose component, the amylopectin component or both. Advantageously, the xylanase added according to the invention accelerates the retrogradation, so the holding time may be shortened. The end-point is conventionally determined by testing the hardness and brittleness of the pellets.

After ageing the rods are cut into pellets.

The drying of the pellets may be done at 70–95° C. for 1–3 hours to reach an exit moisture of 6–8% in the snack pellets.

The dried snack pellets may be stored or distributed to a snack processor. The snack pellets may then be expanded by heating, e.g. by frying in oil or puffing in hot air or in microwave or infrared oven.

Shredded Cereals

According to the invention, shredded cereals may be produced by a process comprising the following sequential steps:
a) mixing a xylanase with cereal-based raw materials,
b) cooking so as to gelatinize starch,
c) cooling and holding to effect retrogradation of the starch,
e) shredding, and
f) baking.

Shredded cereals may be made by cooking whole grain, followed by cooling, tempering, shredding, forming into biscuits and baking.

The whole grain may be wheat (e.g. white wheat), rice or corn. The cooking may be done for 30–35 minutes at atmospheric pressure or 2000 hPa to reach 45–50% moisture after removal of excess water. The holding (or tempering) may take 8–28 hours with cooling to 15–30° C. After shredding, the shreds may be stacked to make a biscuit, and this may be baked at 200–315° C. to around 4% end moisture.

Xylanase

The invention uses a xylanase, i.e. an enzyme having the activity classified as EC 3.2.1.8 according to Enzyme Nomenclature. The enzyme may suitably have a pH optimum in the range 5–9.

The xylanase may have hydrolytic activity on arabinoxylan with a high specificity for soluble arabinoxylan compared to Insoluble arabinoxylan. The specificity may be expressed as WSPS defined as the ratio WSP/WIP described in WO 9523514; the xylanase may have WSPS above 0.1, e.g. above 1.0 or above 2.5. Particular examples are Xylanases I and II from *A. aculeatus* described in WO 9523514.

The enzyme may suitably have a temperature optimum in the presence of starch in the range of 30–90° C., preferably 50–80° C., particularly 55–75° C., e.g. 60–70° C. The temperature optimum may be measured in a 1% solution of soluble starch at pH 5.5.

The enzyme is typically used at a dosage of 0.1–20 mg enzyme protein per kg of dry solids in the raw material, particularly 0.5–5 mg/kg.

The xylanase may be of any origin including mammalian, plant or animal origin, e.g. of microbial origin. In particular the xylanase preparation may be derived from a filamentous fungus or a yeast. More particularly, the xylanase may be derived from a strain of the following genus or species: *Aspergillus, A. niger, A. awamori, A. aculeatus, A. oryzae, A. tubigensis, Trichoderma, T. reesei, T. harzianum, Penicillium, P. camenbertil, Fusarium, F. oxysporum, Thermomyces, T. lanuginosus, Humicola, H. insolens, Bacillus, B. pumilus.*

EXAMPLES

Example 1

Reduction of Storage Period

Rod-type snack pellets were produced with addition of xylanase. The xylanase was Shearzyme, a purified xylanase from *Aspergillus aculeatus* produced by a genetically modified strain of *Aspergillus oryzae* at a dosage of 150 FXU/kg of raw material (the FXU xylanase activity unit is defined in |WO 9404035|). A control was made without addition of xylanase.

The following raw materials were mixed: Potato starch, wheat flour, maize flour, potato granules, salt, paprika, vegetable oil, emulsifier and flavouring.

The raw materials were treated by pre-conditioning at 20–95° C. for 1–2 minutes followed by extrusion at 80–150° C. for 30–90 seconds, and forming at 65–90° C. into long rods.

After forming the rods were placed on racks and stored 16–24 hours before cutting. At the start of ageing the rods were rubber like and did not break when bended. A simple bending test was performed several times during storage, and the rods were judged to be ready for cutting when they readily broke at the bend point when bended.

Finally, the rods were cut and expanded by deep-frying in palm oil at 180° C. for 9–11 seconds.

The results were that the rods made with the xylanase were ready after 18–19 hours whereas the control without endo-amylase was ready after 24 hours. The expanded pellets from the enzyme trials did not show any significant differences compared to the reference on physical parameters.

Example 2

Effect on Snack Texture

Snack pellets were produced according to a sheeted pellet procedure with addition of xylanase. A control was made without xylanase.

The following raw materials were mixed: Potato granules, glucose, salt, vegetable oil, mono- and diglycerides as emulsifiers, and dicalciumphosphate.

The raw materials were treated by preconditioning at 20–80° C. for 1–2 minutes, followed by extrusion at 80–130° C. for 30–45 seconds, forming (sheeting) and drying of the single pellets. The pellets were allowed to rest for at least 24 hours to assure optimal water migration, before expansion. Expansion was done In palm oil at approximately 180° C. for 9–11 seconds.

The texture was judged by a panel of 4 persons. The xylanase, the dosage used and the observed effect were as follows:

| Enzyme | Dosage/kg raw material | Effect |
| --- | --- | --- |
| Xylanase from *Thermomyces lanuginosus* | 2000 FXU | A little firm. No big differences between reference and sample |
| | 5000 FXU | A little firm. No big differences between reference and sample. A little stronger in taste compared to reference, but no bad taste. A very nice product. |

All enzyme-treated products looked nicer than the reference with fewer, smaller and better distributed air bubbles after expansion.

The invention claimed is:

1. A process for producing an edible product, comprising the following sequential steps:
   a) mixing a xylanase with cereal-based raw materials comprising starch,
   b) heating so as to gelatinize the starch,
   c) cooling and holding the starch to effect retrogradation of the starch, and
   d) heating and drying the starch,
   wherein the xylanase accelerates the retrogradation and the holding period is shorter than that required of the same process without added xylanase.

2. The process of claim 1, which further comprises after said step (d), frying the starch in oil.

3. The process of claim 1, wherein the edible product is a snack food or a breakfast cereal.

4. The process of claim 2, wherein the edible product is a snack food or a breakfast cereal.

5. The process of claim 1, which further comprises after said step (d), puffing the starch in hot air.

6. The process of claim 1, which further comprises after said step (d), heating the starch in a microwave oven.

7. The process of claim 1, which further comprises after said step (d), heating the starch in an infrared oven.

8. A process for producing snack pellets, comprising the following sequential steps:
   a) mixing a xylanase with cereal-based raw materials comprising starch,
   b) heating and extruding the mixture so as to gelatinize the starch and form pellets,
   c) cooling and holding the pellets to effect retrogradation of the starch, and
   d) heating and drying the pellets,
   wherein the xylanase accelerates the retrogradation and the holding period is shorter than that required of the same process without added xylanase.

9. The process of claim 8, comprising, following said step (d), frying the pellets in oil.

10. The process of claim 8, which further comprises after said step (d), puffing the starch in hot air.

11. The process of claim 8, which further comprises after said step (d), heating the starch in a microwave oven.

12. The process of claim 8, which further comprises after said step (d), heating the starch in an infrared oven.

13. A process for producing shredded cereals, comprising the following sequential steps:
 a) mixing a xylanase with cereal-based raw materials comprising starch,
 b) cooking the starch so as to gelatinize the starch,
 c) cooling and holding the starch to effect retrogradation of the starch,
 d) shredding the starch, and
 e) baking the starch,
 wherein the xylanase accelerates the retrogradation and the holding period is shorter than that required of the same process without added xylanase.

* * * * *